United States Patent
Banowski et al.

(10) Patent No.: US 10,357,446 B2
(45) Date of Patent: Jul. 23, 2019

(54) COSMETIC ANTIPERSPIRANTS WITH ALKYLSUPHONIC ACIDS

(71) Applicant: Henkel AG & Co. KGaA, Duesseldorf (DE)

(72) Inventors: Bernhard Banowski, Duesseldorf (DE); Marcus Claas, Hilden (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/077,473

(22) Filed: Mar. 22, 2016

(65) Prior Publication Data

US 2016/0199287 A1    Jul. 14, 2016

Related U.S. Application Data

(63) Continuation of application No. PCT/DE2014/200517, filed on Sep. 26, 2014.

(30) Foreign Application Priority Data

Oct. 15, 2013 (DE) .......................... 10 2013 220 783

(51) Int. Cl.
| | | |
|---|---|---|
| *A61K 8/92* | (2006.01) | |
| *A61K 8/26* | (2006.01) | |
| *A61K 8/46* | (2006.01) | |
| *A61Q 15/00* | (2006.01) | |

(52) U.S. Cl.
CPC ................ *A61K 8/92* (2013.01); *A61K 8/26* (2013.01); *A61K 8/466* (2013.01); *A61Q 15/00* (2013.01); *A61K 2800/20* (2013.01)

(58) Field of Classification Search
None
See application file for complete search history.

(56) References Cited

U.S. PATENT DOCUMENTS

| | | | |
|---|---|---|---|
| 2,571,030 A | 10/1951 | Govett et al. | |
| 3,542,919 A | 11/1970 | Buth et al. | |
| 3,553,316 A | 1/1971 | Rubino | |
| 3,887,692 A | 6/1975 | Gilman | |
| 3,904,741 A | 9/1975 | Jones et al. | |
| 3,953,450 A | 4/1976 | Bouillon et al. | |
| 3,991,176 A | 11/1976 | Rubino | |
| 4,017,599 A | 4/1977 | Rubino | |
| 4,359,456 A | 11/1982 | Gosling et al. | |
| 4,775,528 A | 10/1988 | Callaghan et al. | |
| 5,164,177 A * | 11/1992 | Bhatt ..................... | A61K 8/046 424/47 |
| 5,468,473 A * | 11/1995 | Mullen ................... | A61K 8/25 424/66 |
| 5,641,480 A * | 6/1997 | Vermeer ................ | A61K 8/046 424/70.1 |
| 5,643,558 A | 7/1997 | Provancal et al. | |
| 5,851,515 A * | 12/1998 | Esser ....................... | A61K 8/28 424/400 |
| 6,010,688 A | 1/2000 | Shen | |
| 6,042,816 A | 3/2000 | Shen | |
| 6,074,632 A | 6/2000 | Shen | |
| 6,245,325 B1 | 6/2001 | Shen | |
| 6,436,381 B1 | 8/2002 | Carrillo et al. | |
| 6,649,152 B2 | 11/2003 | Carrillo et al. | |
| 6,663,854 B1 | 12/2003 | Shen et al. | |
| 6,923,952 B2 | 8/2005 | Allen et al. | |
| 7,105,691 B2 | 9/2006 | Holerca et al. | |
| 2004/0009133 A1 | 1/2004 | Kolodzik et al. | |
| 2006/0115441 A1 * | 6/2006 | James ..................... | A61K 8/26 424/66 |
| 2008/0069788 A1 | 3/2008 | Roesch | |
| 2009/0175815 A1 * | 7/2009 | Batchelor .............. | A45D 40/04 424/68 |
| 2014/0173833 A1 | 6/2014 | Banowski et al. | |
| 2015/0283047 A1 | 10/2015 | Banowski et al. | |

FOREIGN PATENT DOCUMENTS

| | | | |
|---|---|---|---|
| DE | 102006004957 A1 | | 8/2007 |
| EP | 0183171 A2 | | 6/1986 |
| EP | 0191628 A2 | | 8/1986 |
| EP | 0308937 A2 | | 3/1989 |
| GB | 1347950 | | 2/1974 |
| GB | 1366435 | | 9/1974 |
| GB | 2048229 A | | 12/1980 |
| WO | 2007/059530 A2 | | 5/2007 |
| WO | WO2007059530 | * | 5/2007 |

OTHER PUBLICATIONS

PCT International Search Report (PCT/DE2014/200517) dated Jan. 20, 2015.
Kirk-Othmer, "Encyclopedia of Chemical Technology", Third Edition, vol. 8, pp. 913-916, 1979.

* cited by examiner

*Primary Examiner* — Jennifer A Berrios
(74) *Attorney, Agent, or Firm* — P. Scott Smith

(57) ABSTRACT

The present invention concerns a cosmetic antiperspirant composition comprising at least one substance selected from the group consisting of cosmetic oils which are liquid at 20° C. and 1,013 hPa, odorants and waxes, at least one antiperspirant aluminum salt in a total amount of 1 to 80 wt %, based on the total weight of the cosmetic antiperspirant composition, and at least one compound of the formula (S-I), in which $X^+$ is $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and $R^1$ is a linear or branched, saturated or unsaturated alkyl group having 1 to 10 carbon atoms, the addition of the at least one compound of the formula (S-I) resulting in effective activation of the at least one antiperspirant aluminum salt, in eminent stabilization of this activated state and in outstanding sweat diminution.

8 Claims, No Drawings

COSMETIC ANTIPERSPIRANTS WITH ALKYLSUPHONIC ACIDS

FIELD OF THE INVENTION

The present invention generally relates to a cosmetic antiperspirant, which includes at least one antiperspirant aluminum salt and at least one alkylsulphonic acid, and in which the addition of the at least one alkylsulphonic acid results in an effective activation of the at least one antiperspirant aluminum salt as well as in a stabilization of this activated state and in outstanding sweat diminution.

Furthermore, the present invention relates to the use of a combination of at least one antiperspirant aluminum salt and at least one alkylsulphonic acid to reduce and/or prevent underarm perspiration.

In addition, the present invention relates to a non-therapeutic cosmetic process for preventing and/or reducing the perspiration of the body, in which the antiperspirant product according to the invention is applied to the skin, in particular to the skin of the armpits.

Lastly, the present invention relates to the use of an alkylsulphonic acid to activate and/or stabilize an antiperspirant aluminum salt.

BACKGROUND OF THE INVENTION

The washing, cleaning and caring of one's own body is a basic human need, and modern industry tries continuously to meet these needs of humans in many ways. Of particular importance for daily hygiene is the continuing elimination or at least reduction of body odor and underarm wetness. In the prior art, numerous specific deodorant or antiperspirant body care products are known which have been developed for use in regions of the body having a high density of sweat glands, especially in the armpit area. These are provided in a wide range of administration forms, for example as a powder, in stick form, as an aerosol spray, pump spray, liquid and gel-like roll-on application, cream, gel and as soaked flexible substrates (deodorant wipes).

Cosmetic antiperspirants of the prior art include at least one antiperspirant salt in addition to at least one oil or a fatty substance and an aromatic component or a perfume.

Aluminum halides and aluminum-zirconium halides in the form of chlorides, which are usually basic, are usually used as antiperspirant salt, since they have no skin-irritating effect in contrast to the non-basic aluminum chlorides and aluminum-zirconium chlorides. The disadvantage of the basic aluminum halides and aluminum-zirconium halides, however, lies in the formation of higher molecular weight oligomeric and polymeric aluminum species, which significantly reduce the efficacy of basic aluminum salts and aluminum-zirconium salts in antiperspirants.

For this reason, in the prior art it has been attempted to increase the efficacy of basic aluminum halides and aluminum-zirconium halides by activation, but at the same time maintain good skin compatibility. Documents EP 0308937 A2, EP 0183171 A2, U.S. Pat. No. 4,359,456 A and EP 0191628 A2 thus describe basic aluminum halides and aluminum-zirconium halides, particularly aluminum chlorides, which were obtained by a thermal treatment. The heat-treated activated basic aluminum halides and aluminum-zirconium halides exhibit, in gel permeation chromatography (GPC), a lower percentage of high molecular weight species in comparison to untreated basic aluminum halides and aluminum-zirconium halides and thus an increased efficacy against sweating in antiperspirants.

Furthermore, the efficacy of basic aluminum halides and aluminum-zirconium halides can be increased by incorporating organic acids as complex ligands. Thus, in documents U.S. Pat. Nos. 3,542,919 A, 3,553,316 A, 3,991,176 and WO 2005/092795 A1, methods are disclosed for producing such stabilized aluminum halides and aluminum-zirconium halides which have a higher proportion of short-chain species and are present in activated form.

A disadvantage of the above-mentioned activated basic aluminum halides and aluminum-zirconium halides of the prior art consists in the decrease of the antiperspirant effect with increasing storage time and/or with the use of protic solvents. This is due to the fact that the polymer distribution of the aluminum species is based on a reversible equilibrium, and this equilibrium in protic solvents shifts with increasing time to higher molecular weight aluminum species and therefore to less effective aluminum species.

There is thus a need for cosmetic antiperspirants having no shift in the polymer distribution to long-chain polymers, and thus no significant decrease in the antiperspirant effect, even during long storage periods and/or when using high amounts of protic solvents. Furthermore, the antiperspirants should be inexpensive to produce.

The present invention had the object of providing a cosmetic antiperspirant which avoids or at least mitigates the disadvantages of the prior art, and with which no significant decrease in the activation of antiperspirant aluminum salts occurs during prolonged periods of storage and/or in the presence of protic solvents.

It has now been found, surprisingly, that the use of alkylsulphonic acids or salts thereof in cosmetic products having antiperspirant aluminum salts leads to a significantly increased formation of short-chain aluminum species as well as to an effective stabilization of these short-chain aluminum species even over long periods of storage.

Furthermore, other desirable features and characteristics of the present invention will become apparent from the subsequent detailed description of the invention and the appended claims, taken in conjunction with this background of the invention.

BRIEF SUMMARY OF THE INVENTION

A cosmetic antiperspirant having at least one substance selected from the group of cosmetic oils which are liquid at 20° C. and 1,013 hPa, fragrances and waxes; at least one antiperspirant aluminum salt in a total amount from 1 to 80 wt %, in relation to the total weight of the cosmetic antiperspirant; and at least one compound of formula (S-I)

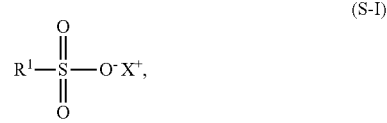

(S-I)

wherein $X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and $R^1$ stands for a linear or branched, saturated or unsaturated alkyl group having 1 to 10 carbon atoms.

Use of a combination of at least one substance selected from the group of cosmetic oils which are liquid at 20° C. and 1,013 hPa, fragrances and waxes, at least one antiperspirant aluminum salt in a total amount from 1 to 80 wt %, in relation to the total weight of the combination, and at least one compound of formula (S-I)

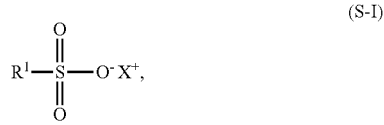

wherein $X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and $R^1$ stands for a linear or branched, saturated or unsaturated alkyl group having 1 to 10 carbon atoms, for reducing and/or preventing perspiration.

Use of at least one compound of formula (S-I)

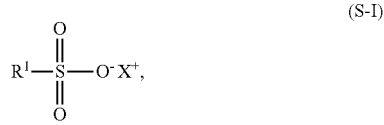

wherein $X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and $R^1$ stands for a linear or branched, saturated or unsaturated alkyl group having 1 to 10 carbon atoms, for activating and/or stabilizing at least one antiperspirant aluminum salt.

A non-therapeutic cosmetic process for preventing and/or reducing the perspiration of the body, in which a cosmetic antiperspirant having at least one substance selected from the group of cosmetic oils which are liquid at 20° C. and 1,013 hPa, fragrances and waxes, at least one antiperspirant aluminum salt in a total amount from 1 to 80 wt %, in relation to the total weight of the cosmetic antiperspirant, and at least one compound of formula (S-1) is applied to the skin, in particular to the skin of armpits.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention relates to a cosmetic antiperspirant having
a) at least one substance selected from the group of cosmetic oils which are liquid at 20° C. and 1,013 hPa, fragrances and waxes,
b) at least one antiperspirant aluminum salt in a total amount from 1 to 80 wt %, in relation to the total weight of the cosmetic antiperspirant, and
c) at least one compound of formula (S-I)

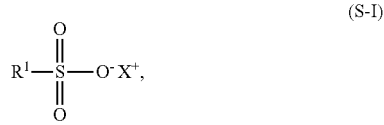

wherein
$X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and $R^1$ stands for a linear or branched, saturated or unsaturated alkyl group having 1 to 10 carbon atoms.

A significant increase in the proportion of short-chain species of the antiperspirant aluminum salts is achieved by combining antiperspirant aluminum salts with specific sulfonic acids of formula (S-I)—without wishing to be limited to this theory. Furthermore, the short-chain species formed in this way are stabilized outstandingly by the aforementioned sulfonic acids, so that an improved antiperspirant effect over a long period is ensured. By using the special sulfonic acids, antiperspirants having a high proportion of protic solvents can be produced in particular, which, in spite of the high amounts of protic solvents, have an excellent antiperspirant effect even during prolonged storage periods.

The term "antiperspirant" is understood in accordance with the invention to mean the decrease or reduction of perspiration of the sweat glands of the body.

Furthermore, the term "cosmetic oil" is understood in the sense of the present invention to mean an oil suitable for cosmetic use, which oil is immiscible with water. Furthermore, the cosmetic oil used in accordance with the invention is constituted neither by fragrances nor by essential oils.

In addition, the term "fragrances" in the sense of the present invention is to be understood to mean substances having a molar mass from 74 to 300 g/mol, which include at least one osmophoric group in the molecule and have an odor and/or taste, i.e. they are able to excite the receptors of the hair cells of the olfactory system. Osmophoric groups are groups covalently bonded to the molecular backbone in the form of hydroxyl groups, formyl groups, oxo groups, alkoxycarbonyl groups, nitrile groups, nitro groups, azide groups, etc. In this context perfume oils, perfumes or perfume oil components liquid at 20° C. and 1,013 hPa also fall under the term "fragrances" in the sense of the present invention.

In addition, the term "waxes" in the scope of the present invention is understood to mean substances which are workable or firm to set hard at 20° C., have a rough to finely crystalline structure and are color-translucent to opaque, but not glass-like. Furthermore, these substances melt above 25° C. without decomposition, are slightly fluid (low viscosity) above the melting point, exhibit a strongly temperature-dependent consistency and solubility, and can be polished under light pressure.

The term "volatile cosmetic oil" means, in accordance with the invention, cosmetic oils that at 20° C. and an ambient pressure of 1,013 hPa have a vapor pressure of 2.66 Pa to 40,000 Pa (0.02 to 300 mm Hg), preferably from 10 to 12,000 Pa (0.1 to 90 mm Hg), more preferably from 13 to 3,000 Pa (0.1 to 23 mm Hg), in particular from 15 to 500 Pa (0.1 to 4 mm Hg).

In addition, the term "non-volatile cosmetic oils" in the sense of the present invention is understood to mean cosmetic oils that at 20° C. and an ambient pressure of 1,013 hPa have a vapor pressure of less than 2.66 Pa (0.02 mm Hg).

Furthermore, the term "fatty acid", as used in the scope of the present invention, is to be understood to mean aliphatic carboxylic acids which have straight or branched carbon groups having 4 to 40 carbon atoms. The fatty acids used within the scope of the present invention can be both naturally occurring and synthetically produced fatty acids. In addition, the fatty acids may be monounsaturated or polyunsaturated.

Lastly, the term "fatty alcohol" within the scope of the present invention is understood to mean aliphatic, monovalent, primary alcohols which have straight or branched hydrocarbon groups having 4 to 40 carbon atoms. The fatty alcohols used within the scope of the invention can also be mono- or polyunsaturated.

The specified wt % used herein refers, unless otherwise specified, to the total weight of the cosmetic antiperspirants according to the invention without optionally present propellant.

In accordance with a preferred embodiment of the present invention the cosmetic oil which is liquid at 20° C. and 1,013 hPa is selected from the group of
(i) volatile cyclic silicone oils, in particular cyclotrisiloxane, cyclotetrasiloxane, cyclopentasiloxane and cyclohexasiloxane, and linear silicone oils having 2 to 10 siloxane units, in particular hexamethyldisiloxane, octamethyltrisiloxane, decamethyltetrasiloxane;
(ii) volatile non-silicone oils, in particular liquid paraffin oils and isoparaffin oils, such as isodecane, isoundecane, isododecane, isotridecane, isotetradecane, isopentadecane, isohexadecane and isoeicosane;
(iii) non-volatile silicone oils, especially higher molecular weight linear polyalkylsiloxanes;
(iv) non-volatile non-silicone oils, in particular the esters of linear or branched saturated or unsaturated $C_{2-30}$ fatty alcohols with linear or branched saturated or unsaturated $C_{2-30}$ fatty acids, which may be hydroxylated, the $C_8$-$C_{22}$ fatty alcohol esters of monovalent or polyvalent $C_2$-$C_7$ hydroxycarboxylic acids, the triethyl citrates, the branched saturated or unsaturated $C_{6-30}$ fatty alcohols, the mono-, di- and triglycerides of linear or branched, saturated or unsaturated, optionally hydroxylated $C_{8-30}$ fatty acids, the dicarboxylic acid esters of linear or branched $C_2$-$C_{10}$ alkanols, the addition products of ethylene oxide and/or propylene oxide with mono- or polyvalent $C_{3-22}$ alkanols, which may be optionally esterified, the symmetrical, asymmetrical or cyclic esters of carbonic acid with fatty alcohols, the esters of dimers of unsaturated $C_{12-22}$ fatty acids with monovalent linear, branched and cyclic $C_{2-18}$ alkanols or $C_{2-6}$ alkanols, the benzoic acid esters of linear or branched $C_{8-22}$ alkanols, such as benzoic acid $C_{12-15}$ alkyl esters and isostearyl benzoate and octyldodecyl benzoate esters, the synthetic hydrocarbons such as polyisobutene and polydecene, the alicyclic hydrocarbons; as well as
(v) mixtures thereof.

The use of volatile silicone oils and volatile non-silicone oils in the cosmetic antiperspirants according to the invention results in a drier skin feel and in a more rapid release of the antiperspirant aluminum salt.

The cyclic volatile silicone oils that can be used within the scope of the invention have at 20° C. and an ambient pressure of 1,013 hPa a vapor pressure from 13 to 15 Pa (0.1 mm Hg). Furthermore, in accordance with the invention, a low-molecular phenyl trimethicone having a vapor pressure of about 2,000 Pa (15 mm Hg) at 20° C. and an ambient pressure of 1,013 hPa can also be used as a linear volatile silicone oil. Due to the high persistence of cyclodimethicones in the environment, however, it may be preferred in accordance with the invention when 0 to less than 1 wt %, preferably 0 to less than 0.1 wt %, of cyclic volatile silicone oils are used in the cosmetic antiperspirant according to the invention.

In accordance with the invention volatile non-silicone oils in the form of $C_{10-13}$ isoparaffin mixtures having a vapor pressure from 10 to 400 Pa (0.08 to 3 mm Hg), preferably from 13 to 100 Pa (0.1 to 0.8 mm Hg), at 20° C. and an ambient pressure of 1,013 hPa are preferably used. Here, it is preferred within the scope of the present invention when the volatile $C_8$-$C_{16}$ isoparaffin is included in a total amount from 1 to 60 wt %, preferably from 3 to 45 wt %, preferably from 5 to 40 wt %, in particular from 8 to 20 wt %, in relation to the total weight of the cosmetic antiperspirant according to the invention. Of course, it is also possible to formulate cosmetic antiperspirants according to the invention with a low proportion of volatile oils—that is to say with 0.5 to 15 wt %, in relation to the total weight of the cosmetic antiperspirant, of volatile oils—or even no volatile oils.

For masking of insoluble components, such as talc or antiperspirant aluminum salts dried on the skin, it may be preferable in accordance with the invention when the cosmetic antiperspirants include a non-volatile silicone oil and/or a non-volatile non-silicone oil.

In this context, cosmetic antiperspirants that are preferred in accordance with the invention include at least one ester of the linear or branched saturated or unsaturated fatty alcohols having 2 to 30 carbon atoms with linear or branched saturated or unsaturated fatty acids having 2 to 30 carbon atoms, which may be hydroxylated, in a total amount from 1 to 30 wt %, preferably from 5 to 26 wt %, preferably 9 to 24 wt %, in particular from 12 to 17 wt %, in relation to the total weight of the cosmetic antiperspirant.

Within the scope of the present invention linear polyalkylsiloxanes having a kinematic viscosity at 25° C. from 5 to 2,000 cSt, especially linear polydimethylsiloxanes having a kinematic viscosity at 25° C. from 5 to 2000 cSt, preferably from 10 to 350 cSt, in particular from 50 to 100 cSt, can be used as non-volatile silicone oils. The aforementioned non-volatile silicone oils are available under the commercial names Dow Corning® 200 or Xiameter PMX from Dow Corning or Xiameter. Further preferred non-volatile silicone oils are phenyl trimethicones having a kinematic viscosity at 25° C. from 10 to 100 cSt, preferably from 15 to 30 cSt, and cetyldimethicones.

The use of mixtures of the abovementioned cosmetic oils, in particular of non-volatile and volatile cosmetic oils, is also preferred in accordance with the invention, since parameters such as skin feel, visibility of the residue and stability of the cosmetic antiperspirant according to the invention can be adjusted in this way, and the product can thus be better customized to the needs of the consumer.

Within the scope of the present invention it is preferred when the cosmetic oil which is liquid at 20° C. and 1,013 hPa is included in a total amount from 1 to 95 wt %, preferably from 10 to 85 wt %, preferably from 20 to 75 wt %, further preferably from 35 to 70 wt %, in particular 50 to 60 wt %, in relation to the total weight of the cosmetic antiperspirant.

However, it may also be preferred when the cosmetic oil which is liquid at 20° C. and 1,013 hPa is included in a total amount from 0.2 to 70 wt %, preferably from 2 to 60 wt %, preferably from 3 to 50 wt %, more preferably from 5 to 35 wt %, in particular from 8 to 20 wt %, in relation to the total weight of the cosmetic antiperspirant. In this context, in accordance with the invention, the antiperspirant compositions according to the invention may also include less than 0.2 wt %, preferably less than 0.1 wt %, especially 0 wt % of the cosmetic oil which is liquid at 20° C. and 1,013 hPa. The use of extremely small amounts of the cosmetic oil which is liquid at 20° C. and 1,013 hPa is particularly preferred in the cosmetic antiperspirants according to the invention, which are present in aqueous, aqueous-alcoholic or aqueous-glycolic form.

In accordance with a preferred embodiment of the present invention the fragrance is selected from the group of (i) esters, in particular, benzyl acetate, phenoxyethyl isobutyrate, p-tert-butylcyclohexyl acetate, linalyl acetate, dimethyl benzyl carbinyl acetate (DMBCA), phenylethyl acetate, benzyl acetate, ethyl methyl phenyl glycinate, allyl cyclohexyl propionate, styrallyl propionate, benzyl salicylate, cyclohexyl salicylate, floramate, melusate and jasmecyclate;
(ii) ethers, in particular benzyl ethyl ethers and ambroxan;
(iii) aldehydes, in particular linear alkanals having 8 to 18 carbon atoms, citral, citronellal, citronellyl oxy acetaldehyde, cyclamen aldehyde, lilial and bourgeonal;
(iv) ketones, especially ionones, alpha-isomethylionone and methyl cedryl ketone;
(v) alcohols, in particular anethole, citronellol, eugenol, geraniol, linalool, phenylethyl alcohol and terpineol;
(vi) hydrocarbons, in particular terpenes such as limonene and pinene; as well as
(vii) mixtures thereof.

However, mixtures of various fragrances are preferably used which together produce an appealing fragrance note.

Cosmetic antiperspirants according to the invention that have a particularly pleasant smell are obtained if the fragrance is included in a total amount from 0.00001 to 10 wt %, preferably from 0.001 to 9 wt %, preferably from 0.01 to 8 wt %, more preferably from 0.5 to 7 wt %, in particular from 1 to 6 wt %, in relation to the total weight of the cosmetic antiperspirant. In this context, however, the fragrance may also be included in a total amount from 0.00001 to 5 wt %, preferably from 0.001 to 4 wt %, preferably 0.01 to 3 wt %, more preferably 0.1 to 2 wt %, in particular 0.2 to 1.5 wt %, in relation to the total weight of the propellant-containing cosmetic antiperspirant.

In accordance with a further preferred embodiment of the present invention the wax is selected from the group of
(i) fatty acid glycerol mono-, di- and triesters;
(ii) butyrospermum parkii (Shea Butter);
(iii) esters of saturated monovalent $C_{8-18}$ alcohols with saturated $C_{12-18}$ monocarboxylic acids;
(iv) linear, primary $C_{12}$-$C_{24}$ alkanols;
(v) esters of a saturated monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate;
(vi) glycerol triesters of saturated linear $C_{12}$-$C_{30}$ carboxylic acids, which may be hydroxylated, in particular hydrogenated palm oil, hydrogenated coconut oil, hydrogenated castor oil, glyceryl tribehenate and glyceryl tri-12-hydroxystearate;
(vii) natural plant waxes, in particular candelilla wax, carnauba wax, Japan wax, sugar cane wax, ouricouri wax, cork wax, sunflower wax, fruit waxes;
(viii) animal waxes, in particular beeswax, shellac wax, and spermaceti;
(ix) synthetic waxes, especially montan ester waxes, hydrogenated jojoba waxes and sasol waxes, polyalkylene waxes and polyethylene glycol waxes, $C_{20}$-$C_{40}$ dialkyl esters of dimer acids, $C_{30-50}$ alkyl beeswax and alkyl esters and alkyl aryl esters of dimer fatty acids, paraffin waxes; as well as
(x) mixtures thereof.

Commercial products with the INCI name cocoglycerides, in particular the commercial products Novata® (ex BASF), more preferably Novata® AB, a mixture of $C_{12-18}$ mono-, di- and triglycerides, which melts in the range from 30 to 32° C., and the products of the Softisan series (Sasol Germany GmbH) with the INCI name hydrogenated cocoglycerides, especially Softisan 100, 133, 134, 138 and 142, are particularly preferred. Further preferred esters of saturated, monovalent $C_{12-18}$ alcohols with saturated $C_{12-18}$ monocarboxylic acids are stearyl laurate, cetearyl stearate (for example Crodamol® CSS), cetyl palmitate (for example Cutina® CP) and myristyl myristate (for example Cetiol® MM). Furthermore, a $C_{20}$-$C_{40}$ alkyl stearate is preferably used as the wax component. This ester is known under the name Kester Wax® K82H or Kester Wax® K80H and is sold by Koster Keunen Inc.

Within the scope of the present invention it is preferred when the wax is included in a total amount from 0.01 to 20 wt %, preferably from 3 to 20 wt %, preferably from 5 to 18 wt %, in particular from 6 to 15 wt %, in relation to the total weight of the cosmetic antiperspirant.

An especially good antiperspirant effect is obtained within the scope of the present invention when the antiperspirant aluminum salt is included in a total amount from 2 to 40 wt %, preferably from 3 to 35 wt %, preferably from 4 to 32 wt %, more preferably from 5 to 28 wt %, still more preferably from 8 to 25 wt %, in particular from 12 to 22 wt %, in relation to the total weight of the cosmetic antiperspirant. However, the antiperspirant aluminum salt may also be included in a total amount from 0.1 to 20 wt %, preferably from 0.5 to 15 wt %, preferably from 1 to 12 wt %, more preferably from 1.5 to 10 wt %, particularly from 2 to 8 wt %, in relation to the total weight of the propellant-containing antiperspirant composition.

Within the scope of the present invention the antiperspirant aluminum salt may be selected from the group of
(i) water-soluble astringent inorganic salts of aluminum, in particular aluminum chlorohydrate, aluminum sesquichlorohydrate, aluminum dichlorohydrate, aluminum hydroxide, potassium aluminum sulfate, aluminum bromohydrate, aluminum chloride, aluminum sulfate;
(ii) water-soluble astringent organic salts of aluminum, in particular aluminum chlorohydrex propylene glycol, aluminum chlorohydrex polyethylene glycol, aluminum propylene glycol complexes, aluminum sesquichlorohydrex propylene glycol, aluminum sesquichlorohydrex polyethylene glycol, aluminum propylene glycol dichlorohydrex, aluminum polyethylene glycol dichlorohydrex, aluminum undecylenoyl collagen amino acid, sodium aluminum lactate, sodium aluminum chlorohydroxylactate, aluminum lipo-amino acids, aluminum lactate, aluminum chlorohydroxyallantoinate, sodium aluminum chlorohydroxylactate;
(iii) water-soluble astringent inorganic aluminum-zirconium salts, especially aluminum zirconium trichlorohydrate, aluminum zirconium tetrachlorohydrate, aluminum zirconium pentachlorohydrate, aluminum zirconium octachlorohydrate;
(iv) water-soluble astringent organic aluminum-zirconium salts, in particular aluminum zirconium propylene glycol complexes, aluminum zirconium trichlorohydrex glycine, aluminum zirconium tetrachlorohydrex glycine, aluminum zirconium pentachlorohydrex glycine, aluminum zirconium octachlorohydrex glycine; as well as
(v) mixtures thereof.

The term "antiperspirant aluminum salts" in accordance with the invention is understood to rule out aluminosilicates and zeolites. Furthermore, in accordance with the invention, water-soluble aluminum salts are understood to mean salts that have a solubility of at least 3 wt % at 20° C., i.e. dissolve at least 3 g of antiperspirant aluminum salt in 97 g of water at 20° C.

Particularly preferred inorganic aluminum salts are selected from aluminum chlorohydrate, in particular aluminum chlorohydrate having the general formula [Al$_2$(OH)

$_5$Cl.1-6H$_2$O]$_n$, preferably [Al$_2$(OH)$_5$Cl.2-3H$_2$O]$_n$, which may be present in unactivated (polymerized) or in activated (depolymerized) form, as well as aluminum chlorohydrate having the general formula [Al$_2$(OH)$_4$Cl$_2$.1-6H$_2$O]$_n$, preferably [Al$_2$(OH)$_4$Cl$_2$.2-3H$_2$O]$_n$, which may be present in unactivated (polymerized) or in activated (depolymerized) form. The preparation of such antiperspirant aluminum salts is disclosed for example in documents U.S. Pat. No. 3,887,692 A, 3,904,741 A, 4,359,456 A, GB 2048229 A and GB 1347950 A.

Antiperspirant aluminum salts selected from what are known as "activated" aluminum salts, which are also referred to as antiperspirant active ingredients "with enhanced activity", are particularly preferred in accordance with the invention. Such active ingredients are known in the prior art and also commercially available. The preparation thereof is disclosed, for example, in documents GB 2048229 A, U.S. Pat. Nos. 4,775,528 A and 6,010,688 A. Activated aluminum salts are usually produced by heat treatment of a diluted solution of the corresponding salt (for example a solution with 10 wt % salt) in order to increase the HPLC peak 4-to-peak 3 area ratio thereof. The activated salt may then be dried to a powder, especially spray-dried. In addition to the spray drying, roller drying is also suitable for example. Activated aluminum salts typically have an HPLC peak 4-to-peak 3 area ratio of at least 0.4, preferably of at least 0.7, especially at least 0.9, wherein at least 70% of the aluminum is to be attributed to these HPLC peaks.

In this context, "activated" aluminum-zirconium salts are also known, having a high HPLC peak 5 aluminum content, in particular a peak 5 area of at least 33%, preferably at least 45%, based on the total area under peaks 2 to 5, as measured by HPLC of a 10 wt % aqueous solution of the active ingredient under conditions in which the aluminum species are dissolved in at least 4 successive following peaks (denoted peaks 2 to 5). Preferred aluminum-zirconium salts having a high HPLC peak 5 aluminum content (also referred to as "ESAZCH") are disclosed for example in documents U.S. Pat. Nos. 6,436,381 A and 6,649,152 A. Furthermore, the aforementioned activated aluminum-zirconium salt can be stabilized additionally with a water-soluble strontium salt and/or with a water-soluble calcium salt, as are disclosed for example in document U.S. Pat. No. 6,923,952 A.

It is also possible in accordance with the invention to use antiperspirant aluminum salts as non-aqueous solutions or solubilizates of an activated antiperspirant aluminum salt or aluminum-zirconium salt, for example, in accordance with document U.S. Pat. No. 6,010,688 A. Such aluminum or aluminum-zirconium salts are stabilized against the loss of activation of the salt by the addition of an effective amount of a polyvalent alcohol having 3 to 6 carbon atoms and 3 to 6 hydroxyl groups, preferably propylene glycol, sorbitol and pentaerythritol.

Complexes of activated antiperspirant aluminum or aluminum-zirconium salts with a polyvalent alcohol having 20 to 50 wt %, preferably 20 to 42 wt %, of activated antiperspirant aluminum or aluminum-zirconium salt and 2 to 16 wt % of molecularly bound water, wherein the balance to 100 wt % is at least one polyvalent alcohol having 3 to 6 carbon atoms and 3 to 6 hydroxyl groups, are also particularly preferred. Propylene glycol, propylene glycol/sorbitol mixtures and propylene glycol/pentaerythritol mixtures are preferred such alcohols. Such preferred complexes in accordance with the invention of an activated antiperspirant aluminum or aluminum-zirconium salt with a polyvalent alcohol are disclosed for example in documents U.S. Pat. Nos. 5,643,558 A and 6,245,325 A.

Within the scope of the present invention it is also possible to use basic calcium-aluminum salts as antiperspirant aluminum salts, as disclosed for example in document U.S. Pat. No. 2,571,030 A. These salts can be obtained by reacting calcium carbonate with aluminum chlorohydroxide or aluminum chloride and aluminum powder or by adding calcium chloride dihydrate to aluminum chlorohydroxide. However, it is also possible to use aluminum-zirconium complexes which are buffered with salts of amino acids, in particular alkaline and alkaline earth glycinates, and as are disclosed for example in document U.S. Pat. No. 4,017,599 A.

Aluminum salts or aluminum-zirconium salts specified in the following documents U.S. Pat. Nos. 6,245,325 A, 6,042,816 A, 6,245,325 A, 6,042,816 A, 6,245,325 A, 6,042,816 A, 6,245,325 A, 6,042,816 A or 7,105,691 A, which are preferably stabilized by amino acids, in particular glycine, hydroxyalkanoic acids, in particular glycolic acid and lactic acid, or betaines, can also be used as preferred antiperspirant activated aluminum salts and aluminum zirconium salts in accordance with the invention.

Further preferred activated aluminum salts are those having the general formula Al$_2$(OH)$_{6-a}$Xa wherein X stands for Cl, Br, I or NO$_3$, and "a" is a number from 0.3 to 5, preferably from 0.8 to 2.5, in particular from 1 to 2, so that the molar ratio of Al:X is 0.9:1 to 2.1:1. Such activated antiperspirant aluminum salts are disclosed for example in document U.S. Pat. No. 6,074,632 A. Particularly preferred is aluminum chlorohydrate (i.e. X stands for Cl in the above formula), and especially 5/6 basic aluminum chlorohydrate with "a"=1, so that the molar ratio of aluminum to chlorine is 1.9:1 to 2.1:1.

Preferred activated aluminum-zirconium salts are those of the general formula ZrO(OH)$_{2-pb}$Y$_b$, wherein Y stands for Cl, Br, I, NO$_3$ or SO$_4$, b is a rational number from 0.8 to 2, and p is the valence of Y, such that the Al:Zr molar ratio is from 2 to 10 and the metal:(X+Y) ratio is from 0.73 to 2.1, preferably from 0.9 to 1.5. Such activated antiperspirant aluminum-zirconium salts are disclosed for example in the aforementioned document U.S. Pat. No. 6,074,632 A. A particularly preferred salt is aluminum-zirconium chlorohydrate (i.e. X and Y stand for Cl), which has an Al:Zr ratio from 2 to 10 and a molar metal:Cl ratio from 0.9 to 2.1. Preferred antiperspirant active ingredients are disclosed in documents U.S. Pat. No. 6,663,854 A and US 2004/0009133 A1.

In accordance with the invention particularly preferred antiperspirant aluminum salts have a molar metal-to-chloride ratio from 1.9 to 2.1. The metal-to-chloride ratio of aluminum sesquichlorohydrates, which are also particularly preferred within the scope of the invention, is 1.5:1 to 1.8:1. Preferred aluminum-zirconium tetrachlorohydrates have a molar ratio of Al:Zr from 2 to 6 and of metal:chloride from 0.9 to 1.3, wherein, in particular, salts with a metal-to chloride molar ratio from 0.9 to 1.1, preferably from 0.9 to 1.0, are preferred.

Within the scope of the present invention a particularly high efficacy and a significantly improved stabilization of the antiperspirant aluminum salt is achieved when the compound of formula (S-I) is included in a total amount from 0.05 to 8 wt %, preferably from 0.1 to 7 wt %, preferably from 0.3 to 5 wt %, more preferably from 0.5 to 3 wt %, still more preferably from 0.8 to 2.5 wt %, in particular from 1 to 2 wt %, in relation to the total weight of the cosmetic antiperspirant. Furthermore, within the scope of the present invention the compound of formula (S-1) may be included in a total amount from 0.05 to 35 wt %, preferably from 0.5 to 33 wt %, preferably from 1 to 31 wt %, more preferably from 3 to 29 wt %, still more preferably from 5 to 27 wt %, in particular from 8 to 25 wt %, in relation to the total weight of the cosmetic antiperspirant. However, it is also possible within the scope of the invention that the cosmetic antiperspirants contain the compound of formula (S-1) in a total amount from 0.05 to 20 wt %, preferably 0.3 to 18 wt %, preferably 0.5 to 15 wt %, more preferably from 0.7 to 10 wt %, even more preferably from 1.0 to 9 wt %, particularly from 1.5 to 6 wt %, in relation to the total weight of the propellant-containing cosmetic antiperspirant. Without intending to be limited to this theory, the use of the above-specified amounts of the compound of formula (S-1) results in a significantly increased formation of short-chain polymers of the antiperspirant aluminum salt and thus in an improved antiperspirant effect. In addition, the short-chain polymers of the antiperspirant aluminum salt can be effectively stabilized even in the presence of protic solvents for a long period, so that the use of the compound of formula (S-1) in the amounts mentioned above leads to a significantly improved antiperspirant effect even after prolonged storage time.

Particularly good results in terms of improving the antiperspirant effect are obtained when the cosmetic antiperspirant contains at least one compound of formula (S-1a)

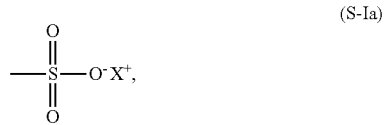

(S-Ia)

wherein,
$X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt.

The combination or mixture of methane sulfonic acid and/or salts thereof (formula S-Ia) with an antiperspirant aluminum salt results in an increased activation of the antiperspirant aluminum salts and furthermore leads to a particularly effective stabilization of the short-chain polymers formed, so that cosmetic antiperspirants according to the invention have a significantly improved antiperspirant effect.

The antiperspirant effect of the cosmetic antiperspirants according to the invention can be further improved if the cosmetic antiperspirant has a weight ratio of the antiperspirant aluminum salt to the compound of formula (S-1) from 40:1 to 19:1, preferably from 30:1 to 16:1, preferably from 20:1 to 15:1, more preferably from 10:1 to 13:1, even more preferably from 9:1 to 12:1, in particular from 8:1 to 1:1. The above-mentioned weight ratio relates to the total amount of all antiperspirant aluminum salts as well as to the total amount of all compounds of formula (S-I) in the cosmetic antiperspirants.

Within the scope of a particularly preferred embodiment the weight ratio of the antiperspirant aluminum salt to the compound of formula (S-1) is 5:1. In addition, the use of a weight ratio of the antiperspirant aluminum salt to the compound of formula (S-1) of 10:1 also leads to cosmetic antiperspirants according to the invention which have an excellent antiperspirant effect, and even after long storage time periods there is no significant degradation of the antiperspirant effect. Furthermore, when using the aforementioned weight ratio, protic solvents can also be used, in particular in high concentrations or quantities, without the antiperspirant effect of the cosmetic antiperspirants according to the invention being adversely affected, so that an extremely flexible packaging of the products according to the invention is possible.

In accordance with a further embodiment of the present invention, the cosmetic antiperspirant does not contain zirconium-containing compounds. The avoidance, in accordance with the invention, of the use of zirconium-containing antiperspirant compounds, such as zirconium-aluminum mixed salts, results in a more cost-effective provision of cosmetic antiperspirants, since the raw materials for the production of zirconium-containing compounds have higher prices.

The cosmetic antiperspirant preferably contains free water in a total amount of less than 10 wt %, preferably of less than 8 wt %, preferably of less than 5 wt %, more preferably of less than 3 wt %, even more preferably of less than 1 wt %, particularly of 0 wt %, in relation to the total weight of the cosmetic antiperspirant. Free water in the sense of the present invention is thus understood to mean water which is different from crystal water, hydration water or similarly molecularly bound water of the constituents used, in particular the antiperspirant aluminum salts.

Surprisingly, it has been found that the amount of short-chain polymers in the combination of an antiperspirant aluminum salt with a compound of formula (S-I) can be significantly increased if the cosmetic antiperspirants according to the invention contain free water in an amount from 15 to 96 wt %, in relation to the total weight of the cosmetic antiperspirant. In a particularly preferred embodiment of the present invention, the cosmetic antiperspirant therefore contains free water in a total amount from 15 to 96 wt %, preferably from 25 to 80 wt %, preferably from 30 to 70 wt %, in particular from 40 to 60 wt %, in relation to the total weight of the cosmetic antiperspirant.

The cosmetic antiperspirants according to the invention are preferably present as suspension of the undissolved antiperspirant aluminum salt in the cosmetic oil which is liquid at 20° C. and 1,013 hPa.

In a further preferred administration form the cosmetic antiperspirants is present as a water-in-oil emulsion. This may in particular be a sprayable water-in-oil emulsion, which can be sprayed by means of a propellant. In this context it is preferable if the cosmetic antiperspirant according to the invention present in the form of a water-in-oil emulsion contains the compound of formula (S-1) in a total amount from 0.05 to 8 wt %, preferably from 0.1 to 7 wt %, preferably from 0.3 to 5 wt %, more preferably from 0.5 to 3 wt %, still more preferably from 0.8 to 2.5 wt %, most particularly from 1 to 2 wt %, in relation to the total weight of the cosmetic antiperspirant.

Within the scope of the present invention the cosmetic antiperspirant may also be present as an oil-in-water emulsion. In this case the product according to the invention is preferably sprayed as a propellant-free pump spray or squeeze spray or is applied as a roll-on. In this context it is preferable if the cosmetic antiperspirant present in the form of an oil-in-water emulsion contains the compound of formula (S-1) in a total amount from 0.05 to 8 wt %, preferably from 0.1 to 7 wt %, preferably from 0.3 to 5 wt %, more preferably from 0.5 to 3 wt %, still more preferably from 0.8 to 2.5 wt %, particularly from 1 to 2 wt %, in relation to the total weight of the cosmetic antiperspirant.

In accordance with the invention the cosmetic antiperspirant may also be present as an aqueous, aqueous-alcoholic or aqueous-glycolic solution. Due to the combination according to the invention of an antiperspirant aluminum salt with a compound of formula (S-I), high quantities of activated aluminum salt can be formed and stabilized, even in protic solvents, such as aqueous solutions, so that in accordance with the invention the use of aqueous cosmetic antiperspirants is also possible, without deactivation of the aluminum antiperspirant salts and thus a significant reduction in the antiperspirant effect.

In accordance with a preferred embodiment of the present invention the antiperspirant cosmetic contains ethanol in a total amount from 1 to 50 wt %, preferably from 5 to 40 wt %, preferably from 7 to 35 wt %, in particular from 10 to 30 wt %, in relation to the total weight of the cosmetic antiperspirant. However, the antiperspirant cosmetic may also contain ethanol in a total amount from 10 to 95 wt %, preferably from 15 to 90 wt %, preferably from 20 to 87 wt %, more preferably from 30 to 85 wt %, in particular from 40 to 80 wt %, in relation to the total weight of the cosmetic antiperspirant. As set forth above, due to the use of the compound of formula (S-I), even high amounts of protic solvents such as ethanol can be used without the activation or stabilization of the short-chain polymers of the antiperspirant aluminum salt being adversely affected.

The cosmetic antiperspirant according to the invention can be applied by various methods. In accordance with a preferred embodiment the cosmetic antiperspirant is provided as a spray application. The spray application is carried out with a spray device which contains, in a container, a filling of the liquid, viscous-flowable, suspension-like or powdered cosmetic antiperspirant according to the invention. The filling may be under the pressure of a propellant (pressurized gas cylinders, pressurized gas dispensers, aerosols), or it can be a mechanically operated pump spray without propellant gas (pump sprays/squeeze bottle). The containers comprise a sampling device, preferably in the form of valves, which allow the removal of the contents as a mist, smoke, foam, powder, paste or liquid jet. In particular, cylindrical vessels made of metal (aluminum, tinplate, volume preferably not more than 1,000 ml), protected or anti-splintering glass or plastic (volume preferably not more than 220 ml) or splintering glass or plastic (volume preferably 50 to 400 ml) constitute potential containers for the spray devices. Creamy, gel-like, pasty and liquid products can be packed for example in pump dispensers, spray dispensers or squeeze dispensers, especially in multi-chamber pump dispensers, multi-chamber spray dispensers, or multi-chamber squeeze dispensers. The packaging for the products according to the invention may be opaque, but also transparent or translucent.

The cosmetic antiperspirant is preferably provided as a stick, soft solid, cream, roll-on, dibenzylidene-based gel, or loose or compact powder. The formulation of the cosmetic antiperspirants according to the invention in a particular administration form, such as an antiperspirant roll-on, an antiperspirant stick or an antiperspirant gel, preferably depends on the requirements of the intended use. Depending on the use the cosmetic antiperspirants according to the invention can therefore be present in solid, semi-solid, liquid, disperse, emulsified, suspended, gel-like, multi-phase or powdered form. The term liquid in the sense of the present invention also includes any type of solid dispersions in liquids. Furthermore, multi-phase cosmetic antiperspirants according to the invention within the sense of the present invention are understood to mean products which have at least 2 different phases with a phase separation and in which the phases can be arranged horizontally, i.e. one above the other, or vertically, i.e. side by side.

The application can be carried out for example using a roller ball applicator. Such rollers have a ball mounted in a spherical bed, which ball can be moved by movement over a surface. In so doing, the ball takes on some of the antiperspirant product to be distributed and transports it to the surface to be treated. The packaging for the products according to the invention can be, as stated above, opaque, transparent or translucent.

Furthermore, it is also possible to apply cosmetic antiperspirants according to the invention by means of a solid stick.

In accordance with the invention, however, it may also be preferred for the cosmetic antiperspirant to be included on and/or in a disposable substrate selected from the group consisting of wipes, pads and wads. Wet wipes are particularly preferred, i.e. ready-to-use wet wipes, preferably individually packaged, as are well known for example from the field of glass cleaning or from the field of wet toilet paper. Such wet wipes, which advantageously can also contain preservatives, are impregnated or loaded with a cosmetic antiperspirant according to the invention and preferably individually packaged. They can be used for example as a deodorant wipe, which is particularly beneficial for use on the go. Preferred substrate materials are selected from porous surface wipes. They may consist of a fibrous or cellular flexible material having sufficient mechanical stability and softness at the same time for application to the skin. These wipes include wipes made of woven and unwoven (non-woven) synthetic and natural fibers, felt, paper or foam, such as hydrophilic polyurethane foam. Deodorant or antiperspirant substrates preferred in accordance with the invention may be obtained by soaking or impregnation or also by melting a cosmetic antiperspirant according to the invention onto a substrate.

The cosmetic antiperspirants according to the invention can also contain other auxiliaries. Cosmetic antiperspirants according to the invention preferably contain at least one broad excipient selected from the group of (i) emulsifiers and/or surfactants; (ii) hydrogel formers; (iii) chelating agents; (iv) deodorant active ingredients; (v) mono- and/or polyvalent alcohols and/or polyethylene glycols; (vi) skin-cooling active ingredients; (vii) propellants; (viii) thickeners and (ix) mixtures thereof.

Suitable emulsifiers and surfactants that are preferred in accordance with the invention are selected from anionic, cationic, non-ionic, amphoteric, especially ampholytic and zwitterionic emulsifiers and surfactants. Surfactants are amphiphilic (bifunctional) compounds which consist of at least one hydrophobic and at least one hydrophilic moiety. The hydrophobic group is preferably a hydrocarbon chain having 8 to 28 carbon atoms which may be saturated or unsaturated, linear or branched. This $C_8$-$C_{28}$ alkyl chain is particularly preferably linear.

Anionic surfactants are understood to be surfactants having solely anionic charges; they contain, for example, carboxyl groups, sulfonic acid groups or sulfate groups. Particularly preferred anionic surfactants are alkyl sulfates, alkyl ether sulfates, acyl glutamates and $C_{8-24}$ carboxylic acids and salts thereof, or what are known as soaps.

Cationic surfactants are understood to be surfactants having solely cationic charges; they contain, for example, quaternary ammonium groups. Cationic surfactants of the quaternary ammonium compound, esterquat and amidoamine type are preferred. Preferred quaternary ammonium compounds are ammonium halides and also the imidazolium compounds known under the INCI names quaternium-27 and quaternium-83. Further cationic surfactants that can be used in accordance with the invention are the quaternized protein hydrolysates. Preferred esterquats are quaternized ester salts of fatty acids with triethanolamine, quaternized ester salts of fatty acids with diethanol alkyl amines and quaternized ester salts of fatty acids with 1,2-dihydroxypropyldialkyl amines.

The amphoteric surfactants are divided into ampholytic surfactants and zwitterionic surfactants. Ampholytic surfactants are understood to be surface-active compounds that have both acid (for example —COOH or —$SO_3H$ groups) and basic hydrophilic groups (for example amino groups) and that thus behave in an acidic or basic manner depending on conditions. Zwitterionic surfactants are understood by a person skilled in the art to mean surfactants that carry both a negative and a positive charge in the same molecule. Examples of preferred zwitterionic surfactants are betaines, N-alkyl-N,N-dimethylammonium glycinates, N-acylaminopropyl-N,N-dimethylammonium glycinates and 2-alkyl-3-carboxymethyl-3-hydroxyethyl-imidazolines with in each case 8 to 24 carbon atoms in the alkyl group. Examples of preferred ampholytic surfactants are N-alkyl glycines, N-alkyl aminopropionic acids, N-alkyl aminobutyric acids, N-alkyliminodipropionic acids, N-hydroxyethyl-N-alkylamidopropyl glycines, N-alkyltaurines N-alkylsarcosines, 2-alkylaminopropionic acids and alkyl aminoacetic acids with in each case 8 to 24 carbon atoms in the alkyl group.

The compositions according to the invention which are formulated as an emulsion, especially an oil-in-water emulsion, preferably contain at least one non-ionic oil-in-water emulsifier with an HLB value of more than 7 to 20. These are emulsifiers generally known to a person skilled in the art, as are listed for example in Kirk-Othmer, "Encyclopedia of Chemical Technology", 3rd edition, 1979, volume 8, page 913-916. For ethoxylated products, the HLB value is calculated according to the formula HLB=(100−L):5, wherein L is the weight proportion of lipophilic groups, i.e. of fatty alkyl or fatty acyl groups in the ethylene oxide adducts, expressed in percentage by weight. In this context, it may be preferable in accordance with the invention if a water-in-oil emulsifier having an HLB value of greater than 1.0 and less than/equal to 7.0 is also used. Within the scope of the present invention, suitable non-ionic oil-in-water emulsifiers and suitable non-ionic water-in-oil emulsifiers are described for example in the German laid-open application DE 102006004957 A1.

For thickening of the cosmetic antiperspirants according to the invention, hydrogel-forming substances are preferably used, selected from cellulose ethers, especially hydroxyalkyl celluloses, in particular hydroxypropyl cellulose, hydroxypropyl methyl cellulose, hydroxyethyl cellulose, carboxymethyl cellulose, cetyl hydroxyethyl cellulose, hydroxybutyl, methyl cellulose, furthermore xanthan gum, sclerotium gum, succinoglucans, polygalactomannans, especially guar gum and locust bean gum, in particular guar gum and locust bean gum itself and the non-ionic hydroxyalkyl guar derivatives and locust bean gum derivatives, such as hydroxypropyl guar, carboxymethyl, hydroxypropyl guar, hydroxypropyl methyl guar, hydroxyethyl guar and carboxymethyl guar, furthermore pectins, agar, carrageenan, tragacanth, gum arabic, karaya gum, tara gum, gellan, gelatin, casein, propylene glycol alginate, alginic acids and salts thereof, in particular sodium alginate, potassium alginate and calcium alginate, furthermore polyvinylpyrrolidones, polyvinyl alcohols, polyacrylamides, furthermore—although less preferred—physically (for example by pregelatinization) and/or chemically modified starches, particularly hydroxypropylated starch phosphates and octenyl starch succinates and their aluminum, calcium or sodium salts, furthermore—likewise less preferred—acrylic acid-acrylate copolymers, acrylic acid-acrylamide copolymers, acrylic acid-vinylpyrrolidone copolymers, acrylic acid-vinyl formamide copolymers, and polyacrylates. Particularly preferred hydrogel formers are selected from cellulose ethers, especially from hydroxyalkyl celluloses, in particular hydroxypropyl cellulose, hydroxypropyl methyl cellulose, hydroxyethyl cellulose, carboxymethyl cellulose, cetyl hydroxyethyl cellulose, hydroxybutyl methyl cellulose and methyl hydroxyethyl cellulose, and mixtures thereof. Hydroxyethyl cellulose is preferably used as hydrogel former.

In order to further support the activating effect of the compound of formula (S-1), it may be advantageous to mix the cosmetic antiperspirants according to the invention with at least one chelating agent selected from ethylenediaminetetraacetic acid (EDTA) and its salts as well as nitrilotriacetic acid (NTA), and mixtures of these substances, in a total amount from 0.01 to 0.5 wt %, preferably from 0.02 to 0.3 wt %, in particular from 0.05 to 0.1 wt %, in relation to the total weight of the antiperspirant product according to the invention. In the present invention, however, chelating agents may also be used which are selected from the group of β-alanine diacetic acid, cyclodextrin, diethylenetriaminepentamethylenephosphonic acid, sodium, potassium, calcium disodium, ammonium and triethanolamine salts of ethylenediaminetetraacetic acid (EDTA), etidronic acid, hydroxyethylethylenediaminetetraacetic acid (HEDTA) and sodium salts thereof, sodium salts of nitrilotriacetic acid (NTA), diethylenetriaminepentaacetic acid, phytic acid, hydroxypropyl cyclodextrin, methylcyclodextrin, pentasodium aminotrimethylene phosphonate, pentasodium ethylenediaminetetramethylenephosphonate, pentasodium diethylenetriaminepentaacetate, pentasodium triphosphate, potassium EDTMP, sodium EDTMP, sodium dihydroxyethyl glycinate, sodium phytate, sodium polydimethylglycinophenol sulphonate, tetra hydroxyethyl ethylenediamine, tetra hydroxypropyl ethylenediamine, tetrapotassium etidronate, tetrasodium etidronate, tetrasodium iminodisuccinate, trisodium ethylenediamine disuccinate and desferrioxamine.

The antiperspirant effect of the cosmetic antiperspirants according to the invention can be increased further if at least one deodorant active ingredient is included in a total amount from 0.0001 to 40 wt %, preferably from 0.2 to 20 wt %, preferably from 1 to 15 wt %, particularly from 1.5 to 5 wt %, in relation to the total weight of the cosmetic antiperspirant according to the invention. If ethanol is used in the products according to the invention, this is, within the scope of the present invention, not as a deodorant active ingredient, but as part of the carrier. Deodorant active ingredients that are preferred in accordance with the invention are selected from the group of (i) silver salts; (ii) aromatic alcohols, especially 2-benzyl-heptan-1-ol, and mixtures of 2-benzylheptan-1-ol and phenoxyethanol; (iii) 1,2-alkanediols having 5 to 12 carbon atoms, especially 3-(2-ethylhexyloxy)-1,2-propanediol; (iv) triethyl citrates; (v) active ingredients against exoesterases, especially against arylsulfatase, lipase, beta-glucuronidase and 3-lyase cystathione; (vi) cationic phospholipids; (vii) an odor absorber, in particular silicates, such as montmorillonite, kaolinite, illite, beidellite, nontronite, saponite, hectorite, bentonite, smectite, and talc, zeolites, zinc ricinoleate, cyclodextrins; (viii) deodorizing ion exchangers; (ix) germ inhibitors; (x) probiotically active components; and (xi) mixtures of these deodorant active ingredients.

Preferred cosmetic antiperspirants according to the invention also contain at least one water-soluble polyvalent $C_{2-9}$ alkanol having 2 to 6 hydroxyl groups and/or at least one water-soluble polyethylene glycol with 3-50 ethylene oxide units, and mixtures thereof. These do not include the aforementioned deodorant active ingredients in the form of 1,2-alkanediols. Preferred alkanols are selected from 1,2-propylene glycol, 2-methyl-1,3-propanediol, glycerol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols, such as 1,2,6-hexanetriol, 1,2-octanediol, 1,8-octanediol, dipropylene glycol, tripropylene glycol, diglycerol, triglycerol, erythritol, sorbitol, cis-1,4-dimethylol cyclohexane, trans-1,4-dimethylol cyclohexane, any isomeric mixtures of cis- and trans-1,4-dimethylol cyclohexane, and mixtures of the aforementioned substances. Suitable water-soluble polyethylene glycols are selected from PEG-3, PEG-4, PEG-6, PEG-7, PEG-8, PEG 9, PEG-10, PEG-12, PEG-14, PEG-16, PEG-18 and PEG-20, and mixtures thereof, wherein PEG-3 to PEG-8 are preferred.

In accordance with another embodiment of the present invention the cosmetic antiperspirants also contain at least one skin-cooling active ingredient. Skin-cooling active ingredients that are suitable in accordance with the invention are, for example, menthol, isopulegol and menthol derivatives, for example menthyl lactate, menthyl glycolate, menthyl ethyl oxamate, menthylpyrrolidone carboxylic acid, menthyl methyl ether, menthoxypropanediol, menthone glycerol acetate (9-methyl-6-(1-methylethyl)-1,4-dioxaspiro (4.5) decan-2-methanol), mono-menthyl succinate, 2-hydroxymethyl-3,5,5-trimethylcyclohexanol and 5-methyl-2-(1-methylethyl) cyclohexyl-N-ethyl oxamate. Menthol, isopulegol, menthyl lactate, menthoxypropanediol, menthylpyrrolidone carboxylic acid and 5-methyl-2-(1-methylethyl)cyclohexyl-N ethyl oxamate and mixtures of these substances, especially mixtures of menthol and menthyl lactate, menthol, menthol glycolate and menthyl lactate, menthol and menthoxypropanediol or menthol and isopulegol, are preferred skin-cooling active ingredients.

Furthermore, cosmetic antiperspirants according to the invention may contain a propellant. In this case they are provided as a propellant-gas-driven aerosol. Preferred propellants (propellant gases) are propane, propene, n-butane, iso-butane, iso-butene, n-pentane, pentene, iso-pentane, iso-pentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, tetrafluoropropene, either individually or in mixtures thereof. Hydrophilic propellant gases, such as carbon dioxide, can also be used advantageously in the sense of the present invention when the proportion of hydrophilic gases is selected to be small and lipophilic propellant gas (for example propane/butane) is present in excess. Propane, n-butane, iso-butane and mixtures of these propellant gases are particularly preferred. It has been shown that the use of n-butane as the sole propellant gas may be particularly preferred in accordance with the invention. The total amount of propellant is 20 to 95 wt %, preferably 30 to 85 wt %, in particular 40 to 75 wt %, in each case in relation to the total weight of the antiperspirant, consisting of the cosmetic antiperspirant according to the invention and the propellant. In this context, the total amount of propellant may be 1 to 95 wt %, preferably 2 to 85 wt %, in particular 3 to 75 wt %, in each case in relation to the total weight of the antiperspirant, consisting of the cosmetic antiperspirant according to the invention and the propellant.

Lipophilic thickeners can also be used as excipients in accordance with the invention. The at least one antiperspirant aluminum salt is preferably suspended undissolved in at least one cosmetic oil which is liquid at 20° C. and 1,013 hPa. For better applicability, at least one lipophilic thickener may also be added as suspension aid to this suspension. Lipophilic thickeners that are preferred in accordance with the invention are selected from hydrophobized clay minerals and fumed silicas.

In a preferred embodiment the cosmetic antiperspirants according to the invention are characterized in that they are provided as water-in-oil emulsion and—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0, 5 to 3 wt %, still more preferably 0.8 to 2.5 wt %, in particular 1 to 2 wt %, 12 to 90 wt %, preferably 25 to 55 wt %, preferably 30 to 50 wt %, in particular 35 to 45 wt % of water, at least one emulsifier and at least one substance selected from the group of cosmetic oils which are liquid at 20° C. and 1,013 hPa, fragrances and waxes.

In a further preferred embodiment cosmetic antiperspirants according to the invention are characterized in that they are provided as oil-in-water emulsion and—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0.5 to 3 wt %, still more preferably 0.8 to 2.5 wt %, in particular 1 to 2 wt %, 15 to 90 wt %, preferably 25 to 55 wt %, preferably 30 to 50 wt %, in particular 35 to 45 wt % of water, at least one emulsifier and at least one substance selected from the group of cosmetic oils which are liquid at 20° C. and 1,013 hPa, fragrances and waxes.

A further preferred embodiment of the present invention comprises cosmetic antiperspirants according to the invention which are characterized in that they—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0.5 to 3 wt %, even more preferably 0.8 to 2.5 wt %, in particular 1 to 2 wt %, 15 to 90 wt %, preferably 25 to 80 wt %, preferably 30 to 75 wt %, in particular 40 to 60 wt % of water, and 0.01 to 2 wt %, preferably 0.1 to 1 wt %, preferably 0.2 to 0.7 wt %, in particular 0.3 to 0.5 wt % of a hydrogel-forming substance.

A further preferred embodiment of the present invention comprises cosmetic antiperspirants according to the invention which are characterized in that they—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0.5 to 3 wt %, even more preferably 0.8 to 2.5 wt %, in particular 1 to 2 wt %, 15 to 90 wt %, preferably 25 to 80 wt %, preferably 30 to 75 wt %, in particular 40 to 60 wt % of water, and 0.01 to 2 wt %, preferably 0.1 to 1 wt %, preferably 0.2 to 0.7 wt %, in particular 0.3 to 0.5 wt % of a hydrogel-forming substance, wherein the cosmetic antiperspirants according to the invention have a dynamic viscosity in the range from 10 to 5000 mPas, preferably from 100 to 1000 mPas, preferably from 200 to 800 mPas, measured with a Brookfield viscometer, spindle RV 4, 20 s$^{-1}$, without Helipath, at 20° C. ambient temperature and 20° C. sample temperature.

A further preferred embodiment of the present invention comprises cosmetic antiperspirants according to the invention which are characterized in that they—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0.5 to 3 wt %, even more preferably 0.8 to 2.5 wt %, in particular 1 to 2 wt %, 15 to 90 wt %, preferably 25 to 80 wt %, preferably 30 to 75 wt %, in particular 40 to 60 wt % of water, and 0.01 to 2 wt %, preferably 0.1 to 1 wt %, preferably 0.2 to 0.7 wt %, in particular 0.3 to 0.5 wt % of a hydrogel-forming substance, wherein the cosmetic antiperspirants according to the invention have a dynamic viscosity in the range from 1,000 to 800,000 mPas, preferably from 2,000 to 700,000 mPas, preferably from 3,000 to 500,000 mPas measured with a Brookfield viscometer, spindle RV 4, 20 s$^{-1}$, without Helipath, at 20° C. ambient temperature and 20° C. sample temperature.

In another preferred embodiment the cosmetic antiperspirants according to the invention are characterized in that they are provided as water-in-oil emulsion and they—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0.5 to 3 wt %, still more preferably 0.8 to 2.5 wt %, in particular 1 to 2 wt %, 15 to 75 wt %, preferably 25 to 60 wt %, preferably 30 to 55 wt %, in particular 35 to 50 wt % of water.

In a further preferred embodiment the cosmetic antiperspirants according to the invention are characterized in that they are provided as oil-in-water emulsion and they—in relation to the total weight of the cosmetic antiperspirant according to the invention—contain at least one antiperspirant aluminum salt in a total amount from 2 to 75 wt %, preferably 3 to 70 wt %, preferably 4 to 65 wt %, more preferably 5 to 55 wt %, still more preferably 8 to 40 wt %, in particular 10 to 30 wt %, at least one compound of formula (S-1) in a total amount of altogether 0.05 to 8 wt %, preferably 0.1 to 7 wt %, preferably 0.3 to 5 wt %, more preferably 0.5 to 3 wt %, still more preferably 0.8 to 2.5 wt %, in particular 1 to 2 wt %, 15 to 90 wt %, preferably 25 to 80 wt %, preferably 30 to 75 wt %, in particular 40 to 60 wt % of water, and optionally 0.01 to 2 wt %, preferably 0.1 to 1 wt %, preferably 0.2 to 0.7 wt %, in particular 0.3 to 0.5 wt % of a hydrogel-forming substance.

A second subject of the present invention is the use of a combination of at least one substance selected from the group of cosmetic oils which are liquid at 20° C. and 1,013 hPa, fragrances and waxes, at least one antiperspirant aluminum salt in a total amount from 1 to 80 wt %, in relation to the total weight of the combination, and at least one compound of formula (S-I)

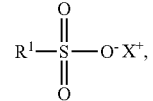

wherein $X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and $R^1$ stands for a linear or branched, saturated or unsaturated alkyl group having 1 to 10 carbon atoms.

for reducing and/or preventing perspiration. The concept of "combination" in the sense of the present invention also comprises a mixture of the at least one substance and the antiperspirant aluminum salt with a compound of formula (S-I). With regard to the use of the aforementioned combination, that stated with regard to the cosmetic antiperspirant applies mutatis mutandis.

Furthermore, a third subject of the present invention is a non-therapeutic cosmetic process for preventing and/or reducing the perspiration of the body, in which a cosmetic antiperspirant having at least one substance selected from the group of cosmetic oils which are liquid at 20° C. and 1,013 hPa, fragrances and waxes, at least one antiperspirant aluminum salt in a total amount from 1 to 80 wt %, in relation to the total weight of the cosmetic antiperspirant, and at least one compound of formula (S-1) is applied to the skin, in particular to the skin of the armpits. With regard to the method according to the invention, that stated with regard to the cosmetic antiperspirant according to the invention and with regard to the use according to the invention applies mutatis mutandis.

Lastly, a fourth subject of the present invention is the use of at least one compound of formula (S-I)

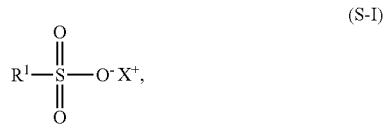

wherein
X+ stands for H+, Li+, Na+, K+, NH4+, ½ Mg2+, ½ Ca2+, ½ Mn2+, ½ Zn2+, ⅓ Al3+, ¼ Zr4+ or at least one antiperspirant aluminum salt and
R1 stands for a linear or branched, saturated or unsaturated alkyl group having 1 to 10 carbon atoms.
for activating and/or stabilizing at least one antiperspirant aluminum salt.

The term activation is understood in the sense of the present invention to mean the significantly increased formation of short-chain polymers of the antiperspirant aluminum salt with use of the compound of formula (S-I).

The term stabilization in the sense of the present invention is furthermore understood to mean the avoidance or the significant slowing in the reformation of higher-chain polymers from the short-chain polymers, formed during activation, of the antiperspirant aluminum salts.

Through the use of specific sulfonic acids of formula (S-I), it is surprisingly possible to significantly increase the activity of antiperspirant aluminum salts even over a longer period of storage. Without intending to be limited to this theory, a significant increase in the proportion of short-chain species of the antiperspirant aluminum salts is achieved by the use of compounds of formula (S-1). Furthermore, the short-chain species formed in this way are stabilized outstandingly by the aforementioned sulfonic acids, so that an improved antiperspirant effect is ensured over a long period.

A particularly good activation and/or stabilization of the at least one antiperspirant aluminum salt is achieved when the compound of formula (S-1) is used in a total amount from 0.01 to 50 wt %, preferably from 0.1 to 40 wt %, preferably from 0.5 to 30 wt %, more preferably from 1 to 20 wt %, still more preferably from 1.5 to 10 wt %, particularly from 2 to 7 wt %, in relation to the total weight of the compound of formula (S-1), the at least one antiperspirant aluminum salt as well as optionally further ingredients. The amounts mentioned above lead to particularly good activation and stabilization of the antiperspirant aluminum salt even over longer storage periods.

In this context it is advantageous if the antiperspirant aluminum salt is used in a total amount from 1 to 99.99 wt %, preferably from 2 to 80 wt %, preferably from 3 to 60 wt %, more preferably from 4 to 50 wt %, in particular from 6 to 45 wt %, in relation to the total weight of the compound of formula (S-1), the at least one antiperspirant aluminum salt as well as optionally further ingredients.

The use of a weight ratio of the antiperspirant aluminum salt to the compound of formula (S-1) from 5.000:1 to 1:0.16, preferably from 1,000:1 to 1:1, preferably from 100:1 to 1:5, more preferably from 50:1 to 1:10, even more preferably from 10:1 to 1:30, in particular from 4:1 to 1:50, has proven to be particularly advantageous for the activation and/or stabilization of the at least one antiperspirant aluminum salt. The above-mentioned weight ratio relates to the total amount of all antiperspirant aluminum salts and all compounds of formula (S-1) in the cosmetic antiperspirants.

Surprisingly, when using the compound of formula (S-I) even in the presence of high amounts of protic solvents such as water, there is a significantly increased activation and/or stabilization of the antiperspirant aluminum salt Therefore, it is preferable when a total amount of free water is used from 1 to 90 wt %, preferably from 5 to 80 wt %, preferably from 10 to 70 wt %, more preferably from 12 to 60 wt %, in particular from 15 to 55 wt %, in relation to the total weight of the compound of formula (S-1), the at least one antiperspirant aluminum salt, the free water and optionally further ingredients.

Furthermore, it is also possible within the scope of the present invention to dry the liquid mixture resulting from the activation and stabilization of the at least one antiperspirant aluminum salt by means of the compound of formula (S-1). This mixture can be dried for example by means of conventional drying methods such as spray drying. The powder obtained in this manner can be stored perfectly and can have a long shelf life.

With regard to further preferred embodiments, that said with regard to the cosmetic antiperspirants according to the invention applies mutatis mutandis.

The following examples illustrate the present invention without being limited thereto:

EXAMPLES

1. HPLC Measurements

To determine the activation of the antiperspirant aluminum salt in the cosmetic antiperspirants, the following aqueous solutions were prepared and stored for 2 or 4 weeks at room temperature (amounts in percentage by weight):
a) stabilization or activation of an already activated aluminum chlorohydrate powder in an aqueous solution (2 weeks of storage at room temperature)

|  | V-I | E-I** | E-II** | E-III** |
|---|---|---|---|---|
| Reach 103, activated aluminum chlorohydrate (ACH) | 10* | 10* | 10* | 10* |
| Methanesulfonic acid (S-Ia) | — | 0.5 | 1 | 2 |
| Water | 90 | 89.5 | 89 | 88 |

*active substance
**according to the invention b) activation of a non-activated aluminum chlorohydrate in an aqueous solution (4 weeks of storage at room temperature)

|  | V-II | E-III** |
|---|---|---|
| non-activated aluminum chlorohydrate (ACH) | 10* | 10* |
| Methanesulfonic acid (S-Ia) | — | 2.0 |
| Water | 90 | 88 |

*active substance
**according to the invention

Such solutions are inter alia representative of hydrous antiperspirant emulsions (antiperspirant roll-ons; antiperspirant sticks, antiperspirant gels, antiperspirant pump sprays).

After 2 and 4 weeks, the activation or stabilization, which results directly from the polymer distribution of samples V-I, V-II, E-I, E-II and E-Ill, was determined by size exclusion chromatography (also referred to as SEC). For this purpose, the respective sample was first diluted to the concentration of 1 g ACH/25 ml of water and filtered (0.2 μm filter). Then, the respective sample was measured using a commercially available HPLC system with a refractive index detector by means of SEC, wherein the following parameters were used:
Flow: 1 ml/min
Temperature: 23° C.
Eluent: 0.02M HCl
Column: 6.2×250 mm, column material: silanized porous silica microspheres (5 µm).

For each sample, 11 or 12 or more peaks were obtained, wherein the peaks with the lower retention time represented the long chain polymers of ACH, and the peaks with higher retention times represented polymers of ACH with shorter chain lengths. The peaks obtained for each sample in the chromatogram were integrated, wherein peaks 2 and 3 (long-chain polymers), 4 to 8 (polymers having medium chain length), 9 to 11 (polymers with short chain length) and 12 as well as all subsequent peaks (very short chain length of the polymers) were integrated together because of shoulders.

The table below specifies the area proportion of peaks 1, 2 to 3, 4 to 8, 9 to 11 and 12 and more in the total area of all peaks obtained for each sample in the chromatogram, which were obtained for the activation or stabilization of an already activated aluminum chlorohydrate powder:

|       | Peak 1 | Peaks 2-3 | Peaks 4-8 | Peaks 9-11 | Peaks 12 and >12 |
|-------|--------|-----------|-----------|------------|------------------|
| V-I   | 0      | 8         | 56        | 31         | 5                |
| E-I   | 0      | 5         | 49        | 38         | 9                |
| E-II  | 0      | 4         | 46        | 38         | 12               |
| E-III | 0      | 4         | 41        | 41         | 14               |

The formulations according to the invention E-I, E-II and E-III have a significantly higher proportion of short-chain polymers (peaks 9 to 12 and more), i.e. a significantly better activation and stabilization, compared with the comparative example V-I. Furthermore, it is apparent from the above table that the polymer distribution can be shifted by increasing the amount of methanesulfonic acid in favor of the short-chain polymers. Consequently, an increase in the amount of methanesulfonic acid results in a further improved activation and stabilization of the already activated aluminum salt used.

For the area proportions of peaks 1, 2 to 3, 4 to 8, 9 to 11 and 12 and more in the total area of all peaks obtained for each sample in the chromatogram for the activation of an already non-activated aluminum chlorohydrate powder, the following values were obtained:

|       | Peak 1 | Peaks 2-3 | Peaks 4-8 | Peaks 9-11 | Peaks 12 and >12 |
|-------|--------|-----------|-----------|------------|------------------|
| V-II  | 6      | 25        | 41        | 28         | 0                |
| E-III | 1      | 7         | 40        | 42         | 10               |

The formulation according to the invention E-IV has a significantly higher proportion of short-chain polymers (peaks 9 to 12 and more), that is to say a significantly improved activation, compared with the comparative example V-II. Furthermore, it is apparent from the above table that the polymer distribution can be shifted by increasing the amount of methanesulfonic acid in favor of the short-chain polymers. Consequently, an increase in the amount of methanesulfonic acid results in a further improved activation of the non-activated aluminum salt used.

2. In Vivo Test for Antiperspirant Effect

To determine the antiperspirant effect an antiperspirant study was carried out on the backs of 18 test subjects. To this end, the following antiperspirant products were used:

| Antiperspirant product | No. |
|---|---|
| Aqueous solution with 10% ACH | V-III |
| Aqueous solution with 10% ACH and 1%* methanesulfonic acid (S-Ia) | E-IV** |
| Aqueous solution with 10% ACH and 2%* methanesulfonic acid (S-Ia) | E-V** |
| W/O emulsion base with 15%* ACH and 15% propanediol | V-IV |
| W/O emulsion base with 15%* ACH and 15% propanediol, 2%* methanesulfonic acid (S-Ia) | E-VI** |

*active substance
**according to the invention

40 µL of the antiperspirant products V-III, E-IV and E-V were applied to the backs of 18 female test subjects aged 35 to 75 years old on one side next to the backbone. After 5 minutes, the treated areas were covered with occlusive non-adsorbent film. After 2 hours, these non-adsorbent pads were removed. The compositions were applied to the backs of test subjects on four consecutive days, in each case in the manner described above. 24 h after the last application of the composition, absorbent pads were applied to the backs of the test subjects at the locations where previously the compositions were applied. Furthermore, pads were also applied to the other side of the backbone at the same height, which served as a control. After the test subjects had been sweating for about 15 minutes at 80° C. in the sauna, the amount of sweat absorbed by the pads was determined gravimetrically, wherein each composition was compared to the respective corresponding untreated position on the back. The sweat diminution was determined from the gravimetric determination of the amount of sweat, wherein all determined values were statistically significant.

In a second study 40 µL of the antiperspirant products V-IV and E-VI were applied to the backs of 18 female test subjects aged 35 to 75 years old, and the procedure as above was followed.

The sweat diminution of the respective composition compared to an untreated skin area is reproduced in the following table:

| No. | Sweat diminution |
|---|---|
| V-III | 47.5% |
| E-IV** | 51.5% |
| E-V** | 63.0% |
| V-IV | 17.3% |
| E-VI** | 30.4% |

By adding methanesulfonic acid (S-Ia), the sweat diminution and thus also the antiperspirant effect is significantly increased. By using a higher amount of methanesulfonic acid a further sweat diminution is possible. Thus, the addition of methanesulfonic acid results in a significantly improved activation and stabilization of the antiperspirant aluminum salt and thus also in a significantly improved sweat diminution of the antiperspirant products according to the invention.

3. Formulations

The following formulation examples are intended to explain the subject of the invention without limiting it in any way. The compound of formula (S-I) used in the examples below is preferably methanesulfonic acid or salts thereof (S-Ia), and mixtures of methane sulfonic acid and salts thereof or mixtures of salts of methanesulfonic acid:

Cosmetic Antiperspirants According to the Invention (Amounts in Wt %)

|  | 1 | 2 | 3 | 4 | 5 | 6 |
|---|---|---|---|---|---|---|
| Hydrogenated Castor Oil | — | — | — | 1.5 | 1.5 | 1.5 |
| Stearyl Alcohol | 24.0 | 24.0 | 24.0 | 18 | 18 | 18 |
| Novata AB | — | — | — | 4 | 4 | 4 |
| Powder of ACH and compound of formula (SI) 15.0 22.0 20.0 11 6 15.6 12.6 (spray-dried, contains 10 wt % (S)) | 15.0 | 22.0 | 20.0 | 11.6 | 15.6 | 12.6 |
| Al-Zr pentachlorohydrex Gly | 7.0 | — | — | 6.00 | — | — |
| PPG-14 Butyl Ether | 10.0 | 10.0 | 10.0 | 15.3 | 15.3 | 15.3 |
| Hydrogenated Castor Oil (for example Cutina HR) | 3.0 | 3.0 | 3.0 | — | — | — |
| Myristyl myristate | 1.5 | 1.5 | 1.5 | — | — | — |
| DL-menthol | 0.2 | 0.2 | 0.2 | — | — | — |
| Eucalyptol | 0.2 | 0.2 | 0.2 | — | — | — |
| Anethole | 0.2 | 0.2 | 0.2 | — | — | — |
| Silica dimethyl silylate | 1.4 | 1.4 | 1.4 | — | — | — |
| Silica | 0.3 | 0.3 | 0.3 | — | — | — |
| Talc | — | — | — | 3 | 3 | 3 |
| Emulgin B1 | — | — | — | 3 | 3 | 3 |
| Perfume | 2.0 | 2.0 | 2.0 | 1 | 1 | 1 |
| Cyclomethicone (at least 95 wt % cyclopentasiloxane) | ad 100 | ad 100 | ad 100 | ad 100 | ad 100 | ad 100 |

Cosmetic Antiperspirants According to the Invention of an Oil-in-Water Emulsion (Amounts in Wt %)

|  | 7 | 8 | 9 |
|---|---|---|---|
| Cutina ® AGS | 2.5 | 2.5 | 2.5 |
| Cutina ® FS45 | 3.5 | 3.5 | 3.5 |
| Eumulgin ® B2 | 0.8 | 0.8 | 0.8 |
| Eumulgin ® B3 | 0.8 | 0.8 | 0.8 |
| Diisopropyladipate | 6.0 | 6.0 | 6.0 |
| Novata ® AB | 4.0 | 4.0 | 4.0 |
| Cutina ® CP | 5.0 | 5.0 | 5.0 |
| Cutina ® HR | 4.0 | 4.0 | 4.0 |
| Kester Wax K62 | 5.0 | 5.0 | 5.0 |
| Locron ® L (ACH solution 50%) | 40 | 40 | 30 |
| Talc Pharma G | 10 | 10 | 10 |
| Perfume | 1.2 | 1.2 | 1.2 |
| 2-Benzylheptan-1-ol | — | 0.3 | 0.3 |
| Sensiva SC 50 | 0.6 | 0.6 | 0.6 |
| Compound of formula (S-I) | 2.0 | 3.0 | 3.0 |
| 1,2-propanediol | 10 | 10 | 10 |
| Water, demineralized | ad 100 | ad 100 | ad 100 |

Cosmetic Antiperspirants According to the Invention in the Form of a Microemulsion (Amounts in Wt %)

|  | 10 | 11 | 12 | 13 |
|---|---|---|---|---|
| Plantaren ® 1200 | 1.7 | 1.7 | — | — |
| Plantaren ® 2000 | 1.1 | 1.4 | 2.4 | 2.4 |
| Glycerol monooleate | 0.71 | 0.71 | — | — |
| Dioctyl ether | 4.0 | 4.0 | 0.090 | 0.090 |
| Octyldodecanol | 1.0 | 1.0 | 0.020 | 0.020 |
| Perfume oil | 1.0 | 1.0 | 1.0 | 1.0 |
| Aluminum chlorohydrate | 8.0 | 5.0 | 5.0 | 10 |
| 1,2-propylene glycol | 5.0 | 5.0 | — | — |
| Glycerol | — | — | 5.0 | 5.0 |
| 2-benzyl-heptane-1-ol | 0.50 | — | — | — |
| triethyl citrate | — | 0.50 | 0.50 | 0.50 |
| Triclosan | 0.10 | — | — | — |
| Compound of formula (S-I) | 1.0 | 2.0 | 2.5 | 2.5 |
| Water | ad 100 | ad 100 | ad 100 | ad 100 |

Cosmetic Antiperspirants According to the Invention in the Form of Roll-Ons (Amounts in Wt %)

|  | 14 | 15 | 16 | 17 |
|---|---|---|---|---|
| Ethanol 96% strength, (DEP denatured) | 30 | 30 | 28 | 28 |
| Mergital ® CS 11 | 2.0 | 2.0 | — | — |
| Eumulgin ® B3 | 2.0 | 2.0 | 2.0 | 2.0 |
| Emulgin ® B1 | — | — | 2.0 | 2.0 |
| Aluminum chlorohydrate 50% (Locron L) | — | 20 | — | 16 |
| Al—Zr pentachlorohydrex Gly | 20 | — | 16 | — |
| Hydroxyethyl cellulose | 0.50 | 0.50 | 0.30 | 0.30 |
| Compound of formula (S-I) | 2.5 | 0.50 | 2.0 | 1.5 |
| EDTA | — | — | — | 0.050 |
| Cocamidopropyl PG-Dimonium Chloride Phosphate | 0.20 | — | — | — |
| Perfume oil | 0.80 | 0.80 | 1.0 | 1.0 |
| Water | ad 100 | ad 100 | ad 100 | ad 100 |

Antiperspirant Wipes

Example Nos. 18 to 21

For the embodiment according to the invention as antiperspirant wipe, a single-layer substrate made of 100% viscose with a basis weight of 50 g/m² was charged with 75 g of the example emulsions 14 and 15 per square meter, or with 75 g of the example compositions 10 and 11, was cut into wipes of appropriate size and was packed in sachets.

Cosmetic Antiperspirants According to the Invention in the Form of a Water-in-Oil Emulsion (Amounts in Wt %)

|  | 22 | 23 | 24 |
|---|---|---|---|
| Aluminum chlorohydrate 50% in water (Locron L) | 35.6 | 35.6 | 20.0 |
| 1,2-propylen glycol | 13.0 | 13.0 | 13.0 |
| cyclohexasiloxane | 6.00 | 6.00 | 6.00 |
| Finosolv TN | 8.00 | 8.00 | 8.00 |
| Abil EM 90 | 1.20 | 1.20 | 1.20 |
| Polyethylene wax (MW = 500 g/mol, Smp = 83 to 91° C.) | 10.0 | 10.0 | 10.0 |

-continued

|  | 22 | 23 | 24 |
|---|---|---|---|
| poly-alpha-olefin wax (MW = 1800 g/mol, Smp = 41° C.) | 0.100 | 0.100 | 0.100 |
| Compound of formula (S-I) | 2.00 | 0.500 | 0.500 |
| EDTA | — | 0.0500 | 0.0500 |
| Water | ad 100 | ad 100 | ad 100 |
| Perfume | 1.00 | 1.00 | 1.00 |

Inventive Cosmetic Antiperspirants (Quantities in Wt %)

|  | 25 | 26 |
|---|---|---|
| Cyclopentasiloxane | 14.0 | 14.0 |
| Abil EM 97 | 3.00 | 3.00 |
| Ethanol 96% | 10.0 | 10.0 |
| Aluminum chlorohydrate 50% in water (Locron L) | 40.0 | 40.0 |
| 1,2-propylene glycol | 20.3 | 20.3 |
| Water | 11.6 | 1106 |
| Compound of formula (S-I) | 2.00 | 0.500 |
| EDTA | — | 0.0750 |
| Perfume | 1.00 | 1.00 |

Cosmetic Antiperspirants According to the Invention (Amounts Given in Wt %, in Relation to the Total Weight of the Propellant-Free Composition)

|  | 27 | 28 | 29 | 30 |
|---|---|---|---|---|
| Aluminum chlorohydrate (ACH) | 28.6 | 14.29 | 32.11 | 28.57 |
| Betone 38 V CG | 5.00 | 3.93 | 4.00 | 5.00 |
| Propylene carbonate | 1.50 | 0.71 | 1.50 | 1.80 |
| Fragrance | 7.14 | 6.50 | 5.00 | 6.50 |
| 2-ethylhexyl palmitate | — | 73.57 | — | — |
| Abil K 4 | 48.4 | — | — | — |
| Isopropyl myristate | 7.37 | — | 10.00 | 19.22 |
| Triethyl citrate | — | — | 10.5 | 19.2 |
| C10-C13 isoalkane | — | — | 35.39 | 19.21 |
| Compound of formula (S-I) | 2.00 | 1.00 | 1.50 | 0.500 |

The example compositions 27 to 30 were filled into an aluminum spray can, optionally coated with epoxy phenolic lacquer, in a weight ratio of propellant (butane/propane/isobutane mixture) to suspension of 80:20 or 85:15 or 60:40 or 90:10.

Cosmetic Antiperspirants According to the Invention (Amounts Given in Wt %, in Relation to the Total Weight of the Propellant-Free Composition)

|  | 31 | 32 | 33 |
|---|---|---|---|
| Aluminum chlorohydrate (ACH) | 33.0 | 33.0 | 33.0 |
| C10-C13 isoalkane | 8.90 | 8.90 | 8.90 |
| Dow Corning ES-5227 DM | 1.40 | 1.40 | 1.40 |
| Isoceteth-20 | 0.500 | 0.500 | 0.500 |
| Dimethicone | 4.20 | 4.20 | 4.20 |
| Isopropyl myristate | 9.00 | 9.00 | 9.00 |
| 1,2-propanediol | 7.00 | 25.0 | 25.0 |
| Phenoxyethanol | 0.500 | 0.500 | 0.500 |
| Perfume | 2.50 | 2.50 | 2.50 |
| Compound of formula (S-I) | 2.00 | 0.500 | 1.50 |
| L-menthol | 0.400 | 0.300 | — |
| Trans-anethole | — | 0.300 | — |
| Eucalyptol | — | 0.300 | — |
| Water | ad 100 | ad 100 | ad 100 |

The example compositions 31 to 33 were filled into an aluminum spray can, optionally coated with epoxy phenolic lacquer, in a weight ratio of propellant (butane/propane/isobutene mixture) to W/O emulsion of 80:20 or 85:15 or 60:40 or 90:10.

Cosmetic Antiperspirants According to the Invention in the Form of O/W Emulsions (Amounts in Weight)

|  | 34 | 35 | 36 |
|---|---|---|---|
| Aluminum chlorohydrate (ACH) | 13.0 | 13.0 | 13.0 |
| Potassium Aluminum sulfate KAl(SO$_4$)$_2$•12H$_2$O | 1.50 | 1.50 | 1.50 |
| Talc | 1.0 | — | — |
| Bentonite | — | 1.00 | — |
| Hectorite | — | — | 5.00 |
| Brij S 2 | 2.50 | 2.50 | 2.50 |
| Brij S 721 | 1.50 | 1.50 | 1.50 |
| Perfume | 1.10 | 1.10 | 1.10 |
| Arlamol E | 0.500 | 0.500 | 0.500 |
| Bisabolol | 0.100 | 0.100 | 0.100 |
| Dry Flo PC | 0.100 | 0.100 | 0.100 |
| Compound of formula (S-I) | 2.00 | 3.00 | 1.00 |
| Dow Corning 2501 Cosmetic Wax | 0.100 | 0.100 | 0.100 |
| Tocopheryl acetate | 0.100 | 0.100 | 0.100 |
| Water | ad 100 | ad 100 | ad 100 |

Cosmetic Antiperspirants According to the Invention (Amounts Given in Wt %, in Relation to the Total Weight of the Propellant-Free Composition)

|  | 37 | 38 | 39 | 40 |
|---|---|---|---|---|
| Aluminum chlorohydrate (ACH) | 33.0 | 33.0 | 33.0 | 33.0 |
| Cyclomethicone | 12.0 | 9.40 | — | — |
| C10-C13 isoalkane | — | — | 9.40 | 8.90 |
| Dow Corning ES-5227 DM | — | 1.40 | 1.40 | 1.40 |
| Abil EM 90 | 3.00 | — | — | — |
| Brij IC 20 | — | — | — | 0.500 |
| Dimethicone | — | 4.20 | 4.20 | 4.20 |
| Isopropyl myristate | 9.00 | 9.00 | 9.00 | 9.00 |
| Compound of formula (S-I) | 2.50 | 1.00 | 3.00 | 0.500 |
| 1,2 propanediol | 7.00 | 7.00 | 7.00 | 7.00 |
| Phenoxy ethanol | 0.500 | 0.500 | 0.500 | 0.500 |
| Perfume | 2.50 | 2.50 | 2.50 | 2.50 |
| Water | ad 100 | ad 100 | ad 100 | ad 100 |

The example compositions 37 to 40 were filled into an aluminum spray can, optionally coated with epoxy phenolic lacquer, in a weight ratio of propellant (butane/propane/isobutene mixture) to W/O emulsion of 80:20 or 85:15 or 60:40 or 90:10.

Cosmetic Antiperspirants According to the Invention in the Form of W/O Emulsions (Amounts in Wt %)

|  | 41 | 42 | 43 | 44 |
|---|---|---|---|---|
| Aluminum chlorohydrate 50% in water (Locron L) | 62.5 | 62.5 | 60.0 | 58.0 |
| Propylene glycol | 5.00 | 5.00 | 7.50 | 9.50 |
| C12-C15 alkyl benzoate | 8.04 | 8.04 | 8.04 | 8.04 |
| Dimethicone 2 cst | 6.43 | 6.43 | 6.43 | 6.43 |
| Dimethicone 5 cst | 4.57 | 1.57 | 1.57 | 1.57 |
| Polyethylene | 10.2 | 11.7 | 9.70 | 12.2 |
| Abil EM 90 | 0.998 | 0.998 | 0.998 | 0.998 |
| Abil EM 97 | 1.22 | 1.22 | 1.22 | 1.22 |
| Compound of formula (S-I) | 2.50 | 1.00 | 3.00 | 0.500 |
| Synthetic wax | 0.100 | 0.100 | 0.100 | 0.100 |
| Perfume | 1.50 | 1.50 | 1.20 | 1.50 |

The following commercial products were used:

| Commercial product | INCI | Supplier/manufacturer |
|---|---|---|
| Abil EM 90 | CETYL PEG/PPG-10/1 Dimethicone | Evonik |
| Abil EM 97 | Bis-PEG/PPG-14/14 Dimethicone, Cyclomethicone | Evonik |
| Abil K 4 | Cyclomethicone | Goldschmidt |
| Arlamol E | PPG-15 Stearyl ether | Croda |
| Bentone 38 VCG | Disteardimonium Hectorite | Elementis Specialities |
| Brij IC 20 | Isoceteth-20 | Croda |
| Brij S 2 | Steareth-2 | Croda |
| Brij S 721 | Steareth-21 | Croda |
| Cutina ® CP | Cetyl Palmitate | BASF |
| Cutina ® FS45 | Palmitic Acid, Stearic Acid | BASF |
| Cutina ® HR | Hydrogenated Castor Oil | BASF |
| Dow Corning ® 245 | Cyclopentasiloxane | Dow Corning |
| Dow Corning ® 2501 | Bis-PEG-18 Methyl Ether Dimethyl Silane | Dow Corning |
| Dow Corning ES-5227 DM | Dimethicone, PEG/PPG-18/18 Dimethicone in weight ration 3:1 | Dow Corning |
| Dry Flo PC | Aluminum Starch Octenylsuccinate | National Starch |
| Eumulgin ® B1 | Ceteareth-12 | BASF |
| Eumulgin ® B2 | Ceteareth-20 | BASF |
| Eumulgin ® B3 | Ceteareth-30 | BASF |
| Kester Wax K62 | Cetearyl Behenate | Koster Keunen |
| Finsolv TN | C12-15 Alkyl Benzoate | Innospec |
| Locron L (AS = 50%) | Aluminum Chlorohydrate | Clariant |
| Mergital ® CS 11 | Ceteareth-11 | BASF |
| Novata ® AB | Cocoglycerides (melting point 30-32° C.) | BASF |
| Plantaren ® 1200 | LAURYL GLUCOSIDE, approximately 50% AS | BASF |
| Planteren ® 2000 | DECYL GLUCOSIDE, approximately 50% AS | BASF |
| Sensiva ® SC 50 | 2-ethylhexyl glycerol ether | Schülke & Mayr |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic antiperspirant, comprising:
   a) at least one oil selected from cosmetic oils which are liquid at 20° C. and 1,013 hPa,
   b) aluminum chlorohydrate in a total amount from 1 to 80 wt %, in relation to the total weight of the cosmetic antiperspirant,
   c) at least one compound of formula (S-Ia)

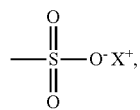
(S-Ia)

wherein $X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, or ¼ $Zr^{4+}$, d) 25 to 80 wt %, in relation to the total weight of the cosmetic antiperspirant, of free water wherein the at least one oil includes a cosmetic oil selected from the group consisting of cyclotrisiloxane, cyclotetrasiloxane, cyclopentasiloxane and cyclohexasiloxane, and hexamethyldisiloxane, octamethyltrisiloxane, and decamethyltetrasiloxane; and wherein the compound of formula (S-1a) is included in a total amount of 1 wt % to 2.0 wt % in relation to the total weight of the cosmetic antiperspirant and wherein the weight ratio of the aluminum salt to the compound of formula (S-Ia) is 8:1 to 1:1.

2. The cosmetic antiperspirant according to claim 1, comprising 0.00001 to 10 wt % of a fragrance in relation to the total weight of the cosmetic antiperspirant.

3. The cosmetic antiperspirant according to claim 1, comprising 0.01 to 20 wt % of a wax in relation to the total weight of the cosmetic antiperspirant.

4. The cosmetic antiperspirant according to claim 1, comprising 3 to 20 wt % of a wax in relation to the total weight of the cosmetic antiperspirant.

5. The cosmetic antiperspirant according to claim 1, further comprising a volatile non-silicone oil selected from the group consisting of isodecane, isoundecane, isododecane, isotridecane, isotetradecane, isopentadecane, isohexadecane and isoeicosane.

6. The cosmetic antiperspirant according to claim 1, further comprising a non-volatile silicone oil
   selected from the group consisting of esters of linear or branched saturated or unsaturated C2-30 fatty alcohols with linear or branched saturated or unsaturated C2-30 fatty acids, which may be hydroxylated, the C8-C22 fatty alcohol esters of monovalent or polyvalent C2-C7 hydroxycarboxylic acids, the triethyl citrates, the branched saturated or unsaturated C6-30 fatty alcohols, the mono-, di- and triglycerides of linear or branched, saturated or unsaturated, hydroxylated C8-30 fatty acids, the dicarboxylic acid esters of linear or branched C2-C10 alkanols, the addition products of ethylene oxide and/or propylene oxide with mono- or polyvalent C3-22 alkanols, the symmetrical, asymmetrical or cyclic esters of carbonic acid with fatty alcohols, the esters of dimers of unsaturated C12-22 fatty acids with monovalent linear, branched and cyclic C2-18 alkanols or C2-6 alkanols, the benzoic acid esters of linear or branched C8-22 alkanols, polyisobutene and polydecene.

7. The cosmetic antiperspirant according to claim 1, wherein the at least one antiperspirant aluminum salt comprises 2 to 40 wt % of the total weight of the cosmetic antiperspirant.

8. A method of activating and/or stabilizing at least one antiperspirant aluminum salt comprising,
   mixing the antiperspirant aluminum salt aluminum chlorohydrate with at least one compound of formula (S-Ia)

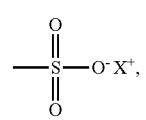
(S-Ia)

wherein
$X^+$ stands for $H^+$, $Li^+$, $Na^+$, $K^+$, $NH_4^+$, ½ $Mg^{2+}$, ½ $Ca^{2+}$, ½ $Mn^{2+}$, ½ $Zn^{2+}$, ⅓ $Al^{3+}$, ¼ $Zr^{4+}$ or at least one antiperspirant aluminum salt and wherein the antiperspirant salt and the at least one compound of formula (S-Ia) are part of a cosmetic antiperspirant that includes at least one cosmetic oil which is liquid at 20° C. and 1,013 hPa, selected from the group consisting of: cyclotrisiloxane, cyclotetrasiloxane, cyclopentasiloxane and cyclohexasiloxane, and hexamethyldisiloxane, octamethyltrisiloxane, and decamethyltetrasiloxane;

wherein the compound of formula (S-Ia) is included in a total amount of 1 wt % to 2.0 wt % and the aluminum chlorohydrate is included in a total amount of 1 to 80 wt %, each in relation to the total weight of the cosmetic antiperspirant;

wherein the weight ratio in the cosmetic antiperspirant of the aluminum salt to the compound of formula (S-Ia) is 8:1 to 1:1; and wherein the cosmetic antiperspirant includes 25 to 80 wt % of free water, in relation to the total weight of the cosmetic antiperspirant.

\* \* \* \* \*